United States Patent
Wing et al.

(10) Patent No.: US 9,291,550 B1
(45) Date of Patent: Mar. 22, 2016

(54) DEVICE AND METHOD FOR INSTANTANEOUS DRUG TESTING IN THE FIELD

(71) Applicants: Nicholas Wing, Nashville, TN (US); Brian Manhire, Hobe Sound, FL (US)

(72) Inventors: Nicholas Wing, Nashville, TN (US); Brian Manhire, Hobe Sound, FL (US)

( * ) Notice: Subject to any disclaimer, the term of this patent is extended or adjusted under 35 U.S.C. 154(b) by 335 days.

(21) Appl. No.: 13/857,392

(22) Filed: Apr. 5, 2013

Related U.S. Application Data

(60) Provisional application No. 61/623,387, filed on Apr. 12, 2012.

(51) Int. Cl.
 *G01N 21/25* (2006.01)
 *G01J 3/44* (2006.01)
 *G01N 21/65* (2006.01)

(52) U.S. Cl.
 CPC .......... *G01N 21/255* (2013.01); *G01J 3/44* (2013.01); *G01N 21/65* (2013.01)

(58) Field of Classification Search
 USPC .......................................................... 348/77
 See application file for complete search history.

(56) References Cited

U.S. PATENT DOCUMENTS

| | | | |
|---|---|---|---|
| 4,659,921 A * | 4/1987 | Alfano | 250/214 VT |
| 4,848,366 A * | 7/1989 | Aita | A41D 13/1192 128/206.24 |
| 4,996,161 A * | 2/1991 | Conners | G01N 33/4972 180/272 |
| 5,807,750 A * | 9/1998 | Baum et al. | 436/164 |
| 5,964,712 A | 10/1999 | Kubo et al. | |
| 6,246,479 B1 * | 6/2001 | Jung | G01J 3/02 250/226 |
| 6,476,856 B1 * | 11/2002 | Zantos | 348/151 |
| 6,609,068 B2 | 8/2003 | Cranley et al. | |
| 6,806,955 B2 * | 10/2004 | Jang | 356/318 |
| 7,052,854 B2 | 5/2006 | Melker et al. | |
| 7,113,814 B2 | 9/2006 | Ward et al. | |
| 7,192,782 B2 | 3/2007 | Roller et al. | |
| 8,248,588 B2 * | 8/2012 | Azimi | G01J 3/02 356/301 |
| 8,300,220 B2 | 10/2012 | Mahadevan-Jansen et al. | |
| 2002/0177232 A1 | 11/2002 | Melker et al. | |
| 2003/0139681 A1 | 7/2003 | Melker et al. | |
| 2003/0216660 A1 | 11/2003 | Ben-Oren et al. | |
| 2005/0234526 A1 | 10/2005 | Gilhuly et al. | |
| 2006/0074282 A1 | 4/2006 | Ward et al. | |
| 2007/0073113 A1 * | 3/2007 | Squilla et al. | 600/300 |
| 2007/0224128 A1 | 9/2007 | Dennis et al. | |
| 2008/0294013 A1 * | 11/2008 | Gobeyn | A61B 5/0059 600/300 |
| 2010/0031963 A1 * | 2/2010 | Lee | A61M 16/06 128/207.11 |
| 2011/0178420 A1 | 7/2011 | Ridder et al. | |
| 2013/0006068 A1 | 1/2013 | Gemer et al. | |

OTHER PUBLICATIONS

Aberl et al., "Traces of illegal drugs on body surfaces—indicator for consumption or dealing?"; 1997; Proceedings of the SPIE—the International Society for Optical Engineering; 2932; 16-26.*

Qu et al.; Screening of Therapeutical Drugs and Substances of Abuse in Human Body Fluids by Near-IR Laser Raman Spectroscopy; Oct. 29-Nov. 1, 1998; IEEE; Engineering in Medicine and Biology Society, 1998. Proceedings of the 20th Annual International Conference of the IEEE; (vol. 4) pp. 1845-1848.*

(Continued)

*Primary Examiner* — Patrick Demosky
(74) *Attorney, Agent, or Firm* — Renner, Kenner, Greive, Bobak, Taylor & Weber

(57) ABSTRACT

A device and method for drug detection with instantaneous results by utilizing a handheld spectroscopic analysis device in an oral, nasal, and upper respiratory examination process.

20 Claims, 5 Drawing Sheets

(56) References Cited

OTHER PUBLICATIONS

Qu et al.; New Method for Screening Drug Addicts Based on Surface-Enhanced Raman Spectroscopy Technology; Jun. 18-20, 2010; IEEE; Bioinformatics and Biomedical Engineering (iCBBE), 2010 4th International Conference on; pp. 1-3.*

Dr. John E. Parmeter, et al., Guide for the Selection of Drug Detectors for Law Enforcement Applications, National Institute of Justice, Aug. 2000, 1-61, National Law Enforcement and Corrections Technology Center, Rockville, MD.

U.S. Department of Transportation, Drug Involvement of Fatally Injured Drivers, NHTSA, Nov. 2010, National Center for Statistics and Analysis, Washington, DC.

Heather M. Eckenrode, et al., Shining New Light on Opaque Polymer, COATINGSTECH, Aug. 2012, 40-45, The Dow Chemical Company, Spring House, PA.

Alain G. Verstraete, Detection Times of Drugs of Abuse in Blood, Urine, and Oral Fluid, Ther Drug Monit, Apr. 2004, 200-2005, vol. 26, No. 2, Lippincott Williams & Wilkins.

Urs Utzinger, et al., Fiber Optic Probes for Biomedical Optical Spectroscopy, Journal of Biomedical Optics, Jan. 2003, 121-147, vol. 8, No. 1, Society of Photo-Optical Instrumentation Engineers, Bellingham, WA.

Brian A. Eckenrode, Portable Raman Spectroscopy Systems for Field Analysis, FBI Forensic Science Communications, Oct. 2002, vol. 4, No. 4.

Timothy J. Johnson, et al., Demonstrated Wavelength Portability of Raman Reference Data for Explosives and Chemical Detection, International Journal of Spectroscopy, Apr. 2012, 1-11, vol. 2012, Article ID 297056, Hindawi Publishing Corporation.

Arthur J. Sedlacek, III, et al., Short-Range, Non-Contact Detection of Surface Contamination Using Raman Lidar, International Society for Optics and Photonics, 2001, 95-104, vol. 4577, Brookhaven National Laboratory, Upton, NY.

Navigant Consulting, Inc., et al., National Lighting Inventory and Energy Consumption Estimate, U.S. Lighting Market Characterization, Sep. 2002, 105-303, vol. 1, U.S. Department of Energy, Washington, DC.

E.C. Cull, et al., Standoff Raman Spectroscopy System for Remote Chemical Detection, International Society for Optics and Photonics, 2005, 1-8, vol. 5994, Duke University Fitzpatrick Center for Photonics and Communications Systems, Durham, NC.

James A. Harrington, Infrared Fiber Optics, International Society for Optics and Photonics, Jun. 1989, 1-3, vol. 1048, Rutgers University, Piscataway, NJ.

David Rouen, et al., A Review of Drug Detection Testing and an Examination of Urine, Hair, Saliva and Sweat, Technical Report No. 120, 2001, 1-61, National Drug and Alcohol Research Centre. University of New South Wales, Sydney.

Briggs, Bill. "Pot fuels surge in drugged driving deaths." NBC News: Health. Feb. 2, 2014. Web. Jun. 6, 2015. <http://www.nbcnews.com/health/health-news/pot-fuels-surge-drugged-driving-deaths-n22991>.

California Legislative Information. "AB-1356 Vehicles: driving under the influence: drug testing." California Legislative Information. Feb. 27, 2015. Web. Apr. 19, 2015. <http://leginfo.legislature.ca.gov/faces/billNavClient.xhtml?bill_id=201520160AB1356>.

DuPont, Robert L., Robert B. Voas, Michael Walsh, Corrine Shea, Stephen K. Talpins, Mark M. Neil. "The Need for Drugged Driving Per Se Laws: A Commentary" Traffic Injury Prevention vol. 13, No. 31-42 (2012).

Flack, Eric. "Drugged Driving Test Kits Being Studied in Louisville." WAVE3 News. Mar. 11, 2015 Web. Mar. 13, 2015. <http://www.wave3.com/story/28358320/drugged-driving-test-kits-being-studied-in-louisville>.

Guohua, Li, Joanne E. Brady, Qixuan Chen. "Drug Use and Fatal Motor Vehicle Crashes: A Case-Control Study." Accident Analysis & Prevention. 60(2013) 205-210. (2013). Web. Nov. 13, 2014.

Harbin, Heather. "'Drug breathalyzer' shot down in committee." KHTS AM 1120. May 5, 2015. Web. May 5, 2015. <http://www.hometownstation.com/santa-clarita-news/politics/drug-breathalyzer-bill-shot-down-in-committee-151125>.

Kerrigan, Sarah. "Drug Toxicology for Prosecutors: Targeting Hardcore Impaired Drivers." American Prosecutors Research Institute (2004). National District Attorneys Association. Web. Nov. 12, 2014.

Laitner, Bill. "Michigan Drug Bill to Drop Roadside Saliva Tests." Detroit Free Press. May 7, 2014. Web. Mar. 15, 2015. < http://www.usatoday.com/story/news/nation/2014/05/07/mich-drug-bills-to-drop-roadside-saliva-tests/8831929/>.

Laser Safety Facts. "Laser Hazard Distance Chart." Lasersafetyfacts.com 2015. Web. Jun. 8, 2015. < http://www.lasersafetyfacts.com/hazard_distance_chart.html>.

Ledbetter, Stewart. "Lawmakers Consider New Technology for Roadside Drug Testing." WPTZ News Channel 5. Apr. 14, 2015. Web. Apr. 14, 2015. <http://www.wptz.com/news/lawmakers-consider-new-technology-for-roadside-drug-testing/32347958>.

Logan, Barry K. Proceedings of a National Meeting of Toxicologists, Drug Recognition Experts and Prosecutors to Identify Problems and Proposed Solutions for Improving Drug-Impaired Driving Prosecution: Priorities and Strategies for Improving the Investigation, Use of Toxicology Results, and Prosecution of Drug-Impaired Driving Cases, findings and recommendations. May 23-25, 2004, NHTSA, U.S., <http://www.nhtsa.gov/people/injury/research/Priorities-Starteg/>.

Massey, Ray. "More than 400 a month arrested for drug driving since new laws introduced: 50% of motorists stopped are testing positive." The Daily Mail. Jun. 11, 2015. Web. Jun. 16, 2015. <http://www.dailymail.co.uk/news/article-3120803/More-400-month-arrested-drug-driving-new-laws-introduced-50-motorists-stopped-testing-positive.html>.

Paducah City Commission Meeting Highlights. SurfKY News. Mar. 11, 2015. Web. Mar. 15, 2015. < http://surfky.com/index.php/news/local/mccracken/58433-paducah-city-commission-meeting-highlights>.

Petroviak, Hunter. "Drivers Under Influence of Drugs on the Rise." WTHI 10 News Feb. 16, 2015. Web. Mar. 15, 2015. <http://wthitv.com/2015/02/16/drivers-under-influence-of-drugs-on-the-rise/>.

Reisfield, Gary M., Bruce A. Goldberger, Mark S. Gold and Robert L. DuPont. "The Mirage of Impairing Drug Concentration Thresholds: A Rationale for Zero Tolerance Per Se Driving under the Influence of Drugs Laws." Journal of Analytical Toxicology. vol. 36, Issue 5, 2012. Web. Nov. 5, 2014.

U.S. Dept. of Transportation—NHTSA. 2007 National Roadside Survey of Alcohol and Drug Use by Drivers. Washington, D.C. 2008. Print.

U.S. Dept. of Transportation—NHTSA. Drug Involvement of Fatally Injured Drivers. Washington, D.C. 2010. Print.

Wanniarachige, Dane. "Drugged Driving: Canada's Laws Lag Behind." Canadian Medical Association Journal. Apr. 14, 2015. Web. Apr. 15, 2015. <http://www.cmaj.ca/site/earlyreleases/14april15_Drugged_driving_Canadas_laws_lag_behind.xhtml>.

We Save Lives. "Drugged Driving." We Save Lives: Drugged Driving Advocacy. (2014). Web. Nov. 11, 2014.

* cited by examiner

DEVICE AND METHOD FOR INSTANTANEOUS DRUG TESTING IN THE FIELD

TECHNICAL FIELD OF THE INVENTION

This invention relates to providing employers and law enforcement with an effective means of instantaneous drug testing in the field by utilizing a handheld spectroscopic analysis device. The invention includes a polymer mask to retrofit existing spectrometric handheld devices for employment, DUI and other drug testing applications in the field.

BACKGROUND OF THE INVENTION

Current employer and law enforcement methods of drug testing in the field do not offer inexpensive, repeatable and instantaneous results. The paucity of available drug testing solutions require the collection of a urine, blood or other biological sample and subsequent off-site laboratory testing. These tests are expensive and require transporting the sample to a laboratory for analysis by a professional technician. According to the National Highway Traffic Safety Administration (NHTSA) National Center for Statistics and Analysis, in 2009, roughly 33% of the 12,055 fatal traffic accidents in the study were found to be caused by a "drugged driver," and further, some states were significantly higher, such as Montana, which found that 77% were caused by drugged drivers (Department of Transportation 2010). There are no national standards for roadside drug testing and the Fatality Analysis Reporting System (FARS) cannot accurately track hit-and-run drugged driving accidents. Law enforcement lacks the tools to effectively mitigate the problem prior to the occurrence of an accident resulting in property damage and/or personal injury, and there is no prevailing roadside drug testing solution that is as reliable as laboratory drug examinations. Unlike, a drunk driver, who may be pulled over and subjected to a breathalyzer examination, a drugged driver, has little fear of being drug tested unless he/she is involved in a traffic accident. Traditional drug testing solutions that require the taking of a biological or breath sample may not meet the Constitutional test under the IV Amendment, protecting the right of the people to be secure against unreasonable searches and seizures, especially when probable cause must be established to utilize a drug test prior to the occurrence of a traffic accident or a moving violation (http://www.gpo.gov/fdsys/pkg/GPO-CONAN-1992/pdf/GPO-CONAN-1992-7.pdf). Therefore, a solution that does not require the collection of a biological sample may more readily meet this Constitutional test and hold up as evidence in the prosecution of DUI drugged driving cases in U.S. court systems. One of the drawbacks of field spectroscopic analysis applications is the unpredictability of environmental and ambient lighting conditions. According to a report commissioned by the U.S. Department of Energy in 2002, *U.S. Lighting Market Characterization*, there were roughly 60 million street light fixtures in operation in the United States (2002). According to the same report, the federal government does not keep a national inventory of the market distribution of these luminaires nor the lighting technology implemented. Environmental and ambient lighting conditions, such as fluorescent lighting and sun light, can interfere with Raman and other forms of spectroscopic analysis, and the presence, dispersal and intensity of these lighting conditions are unpredictable in highway, residential and commercial building environments. Such conditions must be accounted for in a field application of Raman spectroscopic analysis solutions. A standardized and repeatable roadside and employment drug testing solution, which meets the needs of field testing applications, could help to save thousands of lives each year by preventing and effectively deterring drugged driving and substance abuse.

U.S. Pat. No. 8,248,588 B2, which is incorporated by reference herein, teaches an apparatus that includes: (a) an enclosure including an aperture; (b) a prism mounted in the enclosure so that a surface of the prism is exposed through the aperture; (c) an optical assembly contained within the enclosure, the optical assembly including a radiation source and a radiation detector, the source being configured to direct radiation towards the prism and the detector being configured to detect radiation from the source reflected from the exposed surface of the prism; and (d) an electronic processor contained within the enclosure, the electronic processor being in communication with the detector. The apparatus can be configured so that, during operation, the electronic processor determines information about a sample placed in contact with the exposed surface of the prism based on radiation reflected from the exposed prism surface while it is in contact with the sample.

U.S. Pat. No. 8,300,220 B2, which is incorporated by reference herein, teaches a probe using integrated confocal reflectance imaging, confocal Raman spectroscopy, and gross spatial imaging for non-invasively evaluating a target of interest of a living subject. In particular, devices and methods are described that integrate confocal imaging with confocal Raman spectroscopy, for non-invasive evaluation of the biochemical compositions and morphological details of normal and cancerous skin lesions of a living subject.

U.S. Patent Application Pub. No. 2013/0006068 A1, which is incorporated by reference herein, teaches a self-contained drug screening apparatus, comprising a breath inlet component for receiving an exhaled air flow of a person, the exhaled air flow including saliva, and a sensor for sensing a presence of an analyte of interest or drug in the saliva, and identification module for detecting an identifying characteristic of the person.

A lightweight, rugged and portable device is needed that could be employed for accurate, standardized and repeatable roadside and employment field drug testing of a wide spectrum of drugs without taking an invasive sample of breath or saliva and non-invasively examining the interiors of the test subjects mouth and nasal passages without the use of a probe.

SUMMARY OF THE INVENTION

An object of this invention is to provide a rugged field device for in vivo drug detection with instantaneous results, by utilizing a handheld/portable spectroscopic analysis device in an oral, nasal, and upper respiratory examination process.

An object of this invention is to provide a method of in vivo drug detection with instantaneous results by utilizing a handheld/portable spectroscopic analysis device in an oral, nasal, and upper respiratory examination process.

It is another object of the invention to provide a device for inexpensive, repeatable, and highly accurate field drug test that is nonintrusive to the test subject and requires no sample collection nor sample preparation.

It is another object of the invention to provide a device that enables non-technical personnel to administer a drug test without having specialized medical training.

It is another object of the invention to provide a method of determining consumption of controlled substances that provides an unequivocal positive or negative result, such that the results hold up against scrutiny by U.S. and international courts.

It is another object of the invention to provide employers and law enforcement with a device that is capable of instantaneous testing for an array of illegal and prescription drugs, by cross-referencing test results with catalogued spectroscopic signatures of said controlled substances.

The foregoing and other objects of the invention, which shall become apparent as the detailed description proceeds, are achieved by a portable device for instantaneous drug testing for a wide spectrum of drugs that does not require taking an invasive sample of breath or saliva, the device comprising: a flexible, form-fitting opaque mask, adapted to fit snuggly over the mouth and nose region of a test subject who is suspected of drug use; a tube that is connected, at a first end, to the mask with a universal locking fastener, wherein the connection may be optionally reinforced with a locking ring; a swiveling sphere positioned inside the mask and bearing a detector head, wherein the detector head comprises a high definition camera, a source of light for illuminating a target surface within the mouth or nose of the test subject, a plurality of spectroscopic fiber optic heads, and one or more fluorescence blossom detector heads; a spectrometer connected to a second end of the tube, said spectrometer comprising an internal computer, a CCD, an excitation laser, one or more mirrors, optical filters and a user interface that includes receivers for receiving input from a user, and a display for displaying to a user real-time images from the high definition camera and test results from the computer; and a plurality of fiber optic strands extending from the Raman fiber optic heads and fluorescence blossom detector heads, through said tube, into said spectrometer, where each strand is directed toward said CCD.

Other features, details, utilities, and advantages of the present invention may be apparent from the following more particular written description of various embodiments of the invention as further illustrated in the accompanying drawings and defined in the appended claims.

DETAILED DESCRIPTION OF THE PREFERRED EMBODIMENTS

Figure 1:
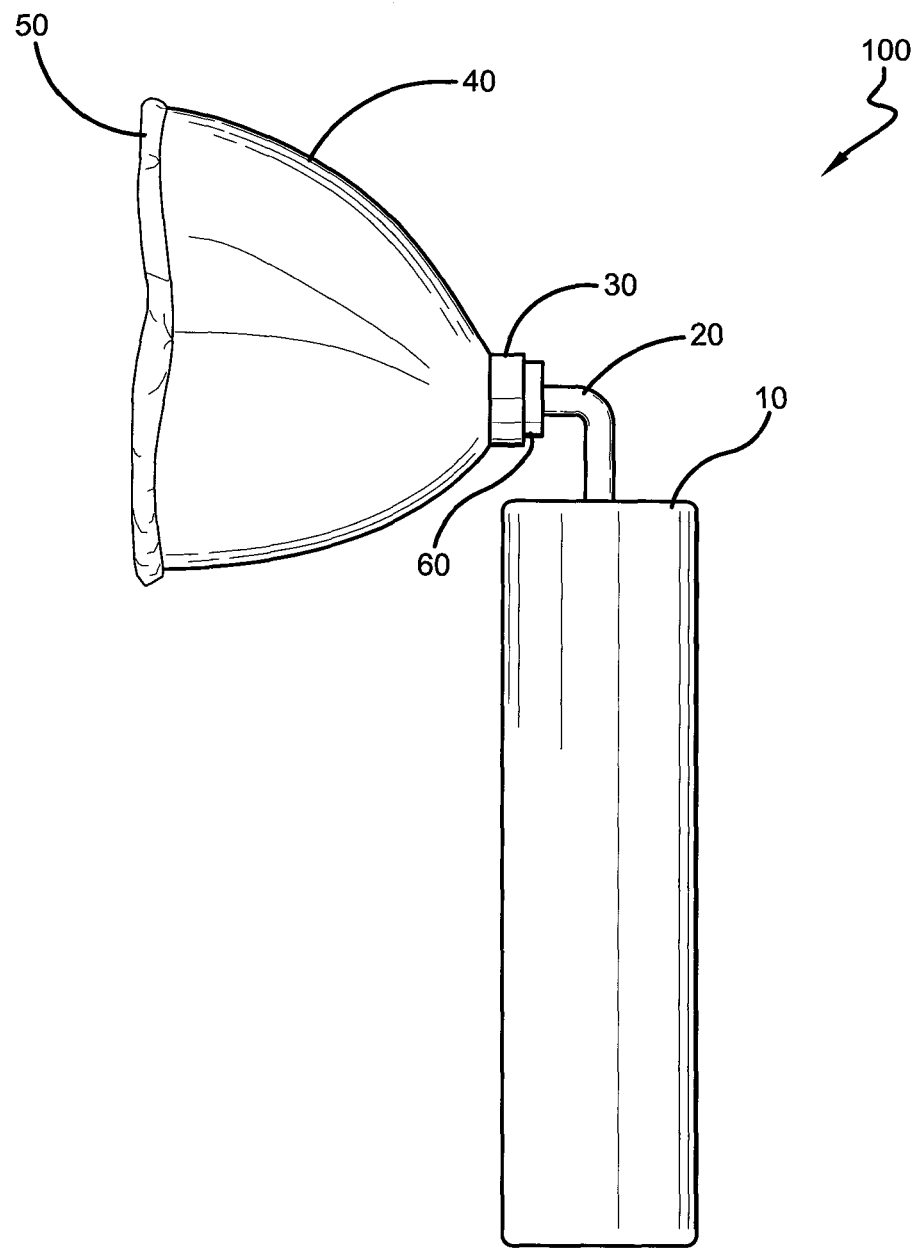
FIG. 1 is a side view of a device according to the present invention.
Figure 2:
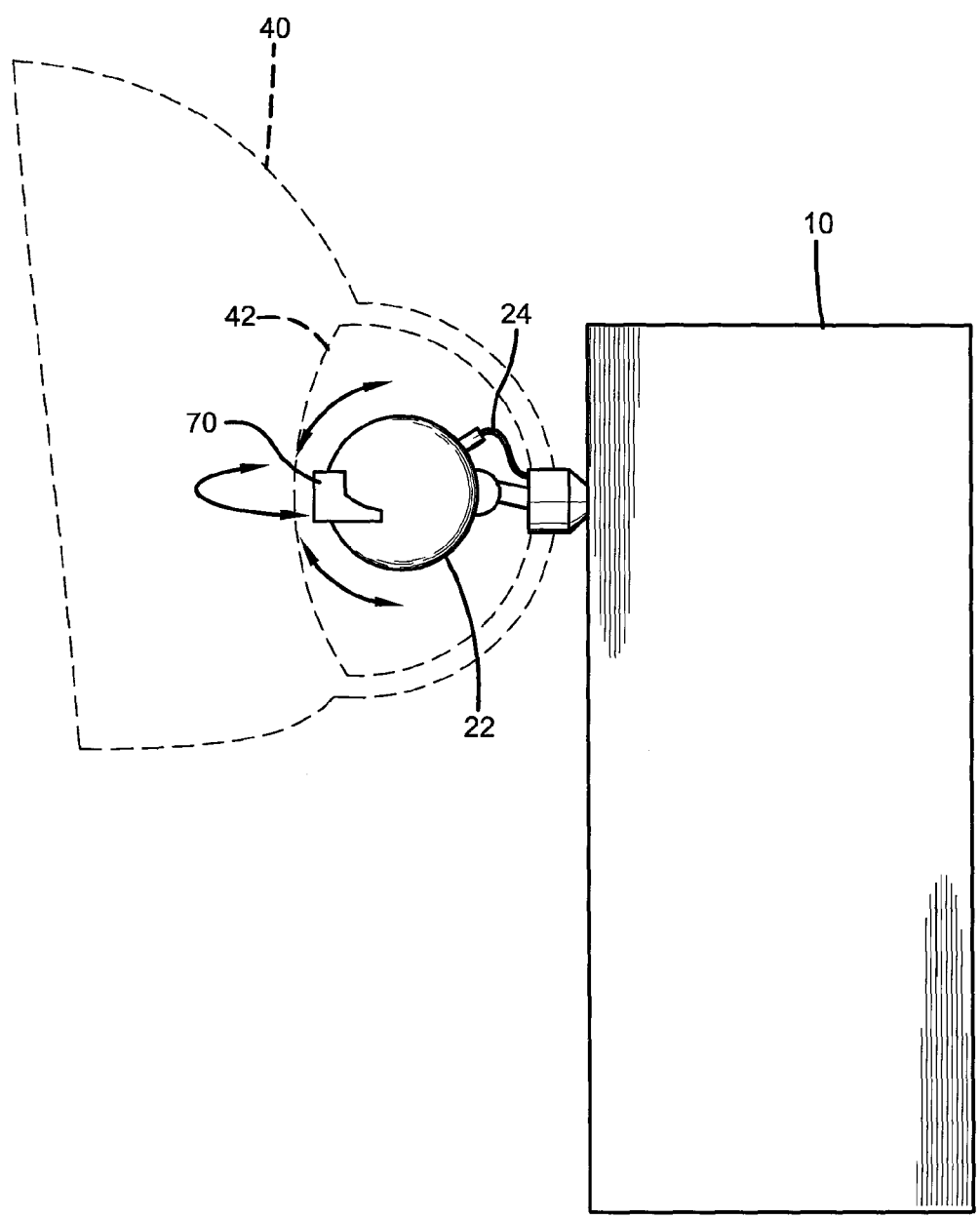
FIG. 2 is a sectional view of a portion of a device according to the present invention, with the mask and shield shown only in outline form, so that the inner portions of the device are visible.
Figure 3:
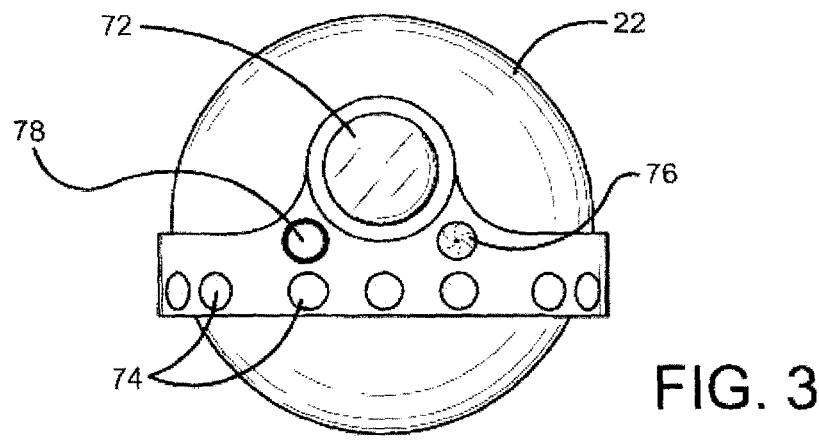
FIG. 3 is a schematic view of the detector head of a device according to the present invention.

A device according to one embodiment of the present invention is shown in FIGS. 1-3. Referring now to FIG. 1, it can be seen that handheld spectroscopic device 100 is provided, and includes spectrometer 10, tube 20 protruding from spectrometer 10, and polymer mask 40, which may be attached to tube 20 by way of universal locking mechanism 30, and optionally reinforced by ring 60.

In one or more embodiments, spectrometer 10 is a handheld spectroscopic device. Handheld spectroscopic devices include those based upon UV, infrared, NIR, fluorescence, Raman, and other types of spectroscopy utilizing a laser(s). Advantageously, in one or more embodiments, commercially available handheld spectroscopic devices may be adapted for use in the method of the present invention. The design and encasement of the spectrometer is robust, rugged and shock absorbing for use in the field.

In one or more embodiments, spectrometer 10 includes a touch screen display, an internal computer, a sensor for sensing environmental/fluorescent light, and a laser light source.

In one or more embodiments, spectrometer 10, when instructed to do so, displays a targeting crosshair(s) for accurate alignment of the laser(s).

In one or more embodiments, tube 20 is a right angle laser lens tube, and extends from spectrometer 10 to mask 40. Examples of right angle laser lens tubes include, but are not limited to, those that are currently employed in TruScan handheld Raman spectrometer, available from Thermo Scientific, and are further described in U.S. Pat. No. 8,248,588 B2.

In one or more embodiments, universal locking apparatus 30 may be employed to attach mask 40 to spectrometer 10. In one or more embodiments, universal locking apparatus 30 may be adapted to attach mask 40 to any existing handheld spectroscopic device.

In one or more embodiments, the device of the present invention includes a robust, yet elastic and form fitting, mask 40. In one or more embodiments, mask 40 is polymeric. In one or more embodiments, mask 40 is opaque. Advantageously, mask 40 overcomes one of the primary drawbacks of Raman spectroscopy in field analysis, namely the interference of extraneous lighting conditions, including sun light and fluorescent light. In one or more embodiments, mask 40 is opaque to fluorescent light.

In one or more embodiments, spectrometer 10 includes a detector for sensing fluorescent and environmental light. If the sensor indicates that the lighting conditions are acceptable for an accurate measurement, the spectrometer's internal computer will activate the laser. In one or more embodiments, the laser of spectrometer 10 will remain disabled by the internal computer until the sensor indicates that the lighting conditions are acceptable for an accurate test, and will remain disabled until ideal lighting conditions are met. In one or more embodiments, the position and/or fit of opaque mask 40 may be adjusted until acceptable lighting conditions are achieved.

In one or more embodiments, mask 40 may include disposable paper cover 50, for proper sanitation when testing a plurality of persons.

Optional ring 60, which may be metallic, may be employed to reinforce a universal locking/clamping apparatus.

As shown in FIG. 2, the device of the present invention further includes detection head 70, which may be mounted on multi-directional swiveling sphere 22 and connected electronically to spectrometer 10. In one or more embodiments, detection head 70 is rounded, and conforms to the shape of swiveling sphere 22, wrapping around, as illustrated in FIG. 2. Fiber optic cables 24 may extend from spectrometer 10 to detection head 70. It should be understood that fiber optic cables 24 include a plurality of fiber optic strands. Separate portions of the strands may be employed to serve distinct functions.

In one or more embodiments, polymer mask 40 encloses detector head 70, fiber optic cable 24, and swiveling sphere 22. In one or more embodiments, an optional plexiglass shield 42 resides within a recessed area of polymer mask 40 and at least partially encloses detector head 70, fiber optic cable 24, and swiveling sphere 22. This enclosure is designed to prevent contact with the test subject being examined.

As shown in FIG. 3, detection head 70 may include a high definition (HD) camera 72, a plurality of Raman fiber optic heads 74, one or more fluorescence blossom detector heads 76, and an opening through which light, such as light used as flash light for cameras, is emitted 78.

Sphere 22 may be rotationally connected to tube 20 via one or more jointed, movable extensions, such that sphere 22 can be moved up, down, forward or backwards, and can rotate in place, all via control of the user through the computer interface of spectrometer 10. In this manner, detection head 70 may be positioned to direct the emitted light toward a target surface, and also the direct camera 72, fiber optic heads 74, and fluorescence detector heads 76 to receive any resulting image and emissions from the target surface. In one or more embodiments, mask 40 may also serve to stabilize the position of the laser diodes and aiming apparatus relative to the target surfaces of the test subjects mouth and nasal passages.

According to one or more embodiments, HD digital camera 72 and flash 78 may be employed for capturing high-resolution images of a test subject's teeth, palate, tongue, gums and nasal passages. Advantageously, any visible remnant of consumed illegal and controlled substances will be captured in these digital photographs. Further, these images will be used to identify the test subject in court and shall provide evidence of biological symptoms and indicators of habitual substance abuse. Such biological indicators include, but are not limited to the following: tooth decay, "meth mouth", hyperkeratosis, "crack mouth", tooth loss, lack of saliva, decreased blood flow to the gums, severe recession of buccal periodontal tissue, acute necrotizing gingivitis, hyperpigmentation of the tongue, gingival lesions, tempromandibular disorders, bruxism, cervical abrasion, occlusal wear, corrosion of gold dental restorations, hemorrhaging, periodontal disease, oral ulcers and perforation of the palate (Tennessee Dental Hygienists Association; Peterson). Indications of habitual substance abuse in the nasal passages have been described in the literature, for example in Karch, Steven B., Olaf Drummer, "Pathology of Drug Abuse: Third Edition," CRC Press LLC, Boca Raton, Fla. (2002). Such indications include, but are not limited to, destruction of the nasal cavity, nasal necrosis, damage to the septal mucosa, discoloration of nasal passage due to necrosis, exposed cartilage, redness, lesions, hemorrhaging and damaged septum. These high definition images will aid the court in the determination of an effective drug treatment plan and adequate sentencing for convicted DUI drugged drivers and repeat offenders.

In one or more embodiments, laser emission from an excitation laser 21 within spectrometer 10 illuminates the remnants of consumed controlled substances on or within a target surface of the gums, teeth, nasal passages, in vivo saliva, in vivo mucus, in vivo gases, etc. In one or more embodiments, a sequence of frequencies are emitted by the excitation laser toward the target surface and the spectral response of the remnants of consumed illegal or controlled substances or biological analytes and indicators of drug consumption to the various frequencies is detected by detection head 70, communicated to spectrometer 10, and recorded by the internal computer. This data can be cross-referenced against an internal database within the internal computer, containing existing spectrometric signatures of controlled and illegal substances that are known either to be illegal or to impair the operator of a motor vehicle.

In an embodiment utilizing Raman spectroscopic analysis, a monochromatic laser diode may be utilized to direct an electromagnetic beam to the target surface. Raman spectroscopic analysis methods may include Stokes (lower frequency vibration) scatter or Anti-Stokes (higher vibration) scatter analysis, as further described in U.S. Pat. No. 8,248,588 B2. In an embodiment utilizing Raman spectroscopic analysis fiber optics will be employed to transmit the laser beam and to receive the spectral response of the target including scattered or absorbed light. Advantageously, and as described in Eckenrode, Harvey, Vucelick, Wright and Huff's Portable Raman Spectroscopy for Field Analysis, FBI Forensic Science Communications, 4, (October 2002), Raman spectroscopic analysis lasers are unaffected by strong IR absorbers such as water, $CO_2$, and silica, no additional accessories are needed for field analysis for aqueous solutions because water is a weak scatterer. According to Eckenrode, Raman lasers are ideal for probing micro-samples, surfaces, films, powders, solutions, gases among other sample types.

In one or more embodiments, Raman spectroscopy may be employed for the examination of in vivo saliva, mucus, gases and other biological indicators of drug consumption, as water and water vapor is a poor scatterer, and therefore less apt to interfere with the accuracy of the examination and its results. As described in Sedlacek, Arthur J., Mark D. Ray, N. S. Higdon and D. A. Richter. "Short-range, Non-contact Detection of Surface Contamination Using Raman Lidar." [0077], a target chemical compound can be accurately and successfully analyzed via stand-off Raman spectroscopy at distances up to 500 meters (2001). In one or more embodiments, stand-off Raman spectroscopy may be utilized to determine the presence and chemical composition of illegal and controlled substance remnants on the target surfaces and within the biological fluids, secretions and gases of the upper respiratory system.

Figure 4:
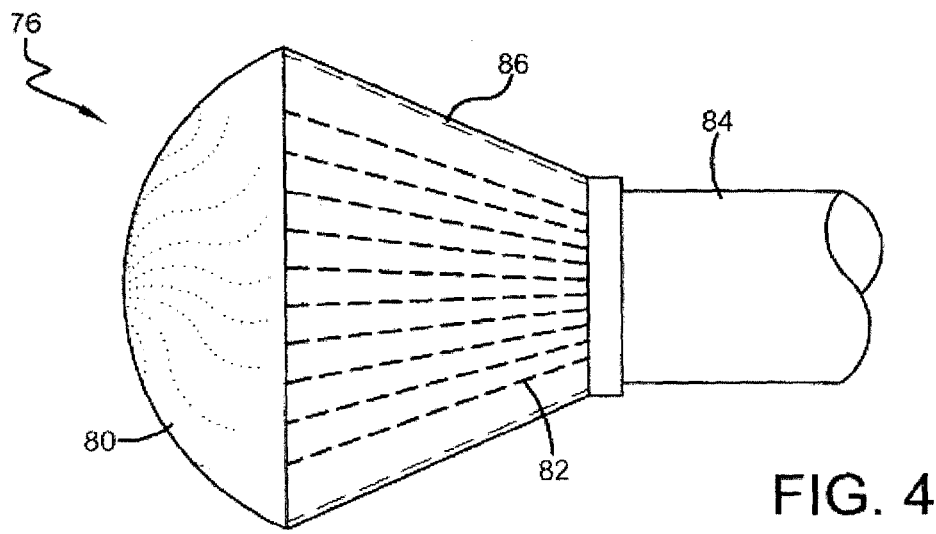
FIG. 4 is a schematic view of a fluorescence blossom detector head according to the present invention.

As illustrated generally in FIG. 4, fluorescent blossom detector 76 includes multiple silica fiber strands 82 that extend from orienter disc 80 through polymer enclosure 86 into shielded fiber optic bundle cover 84 that bundles and covers the strands. It should be noted that fiber strands 82 are separate and distinct from fiber optic cable groupings that are employed for other components of detector head 70. Fiber strands 82 extend through bundle cover 84 whereupon one end of each strand is aimed toward a charged coupled device (CCD) within spectrometer 10. In one or more embodiments, fiber strands 82 will be allotted a region of the CCD surface that is dedicated to the detection of fluorescent light. Advantageously, the blossom detector head may be utilized in other embodiments for capturing the back scattered light from the examination.

According to one embodiment, fluorescence blossom detector 76 may be positioned to appear on detector head 70 to the right of HD camera 72, when looking into mask 40 from the open end.

As described above, one end of each silica fiber strand 82 is directed toward a CCD. Each silica fiber strand 82 has an opposite end, which may be referred to as a silica fiber tip 88. In one or more embodiments, orienter disc 80 includes openings through which silica fiber tips 88 may extend, and orienter disc 80 is thereby able to orient the position of silica fiber tips 88. In one or more embodiments, each silica fiber tip 82 extends through an opening in orienter disc 80, and continues some distance toward the target surface, i.e. the tip protrudes from the outer surface of orienter disc 80 (the outer surface of orienter disc 80 being the surface that is closest to the target surface). In other embodiments, each silica fiber tip 82 extends through an opening in orienter disc 80, but extends no further than the outer surface of orienter disc 80.

Silica fiber tip 88 may be of a standard configuration, or may be shaped. Each tip may be the same, or a variety of different tips may be employed. In one or more embodiments, one or more silica fiber tips are advantageously spherically-shaped to maximize its light collecting efficiency.

In one or more embodiments, silica fiber strands 82 each have a diameter of from about 50 nanometers (nm) to about 500 nm. Further, the return fiber optic cables are individually shielded and are not coupled with other cables in order to preserve the integrity of the signal of each detector fiber optic cable head arranged on the face of the aiming apparatus in order that it can be allotted a dedicated region on the surface of the CCD 96 within spectrometer 10.

Figure 5:
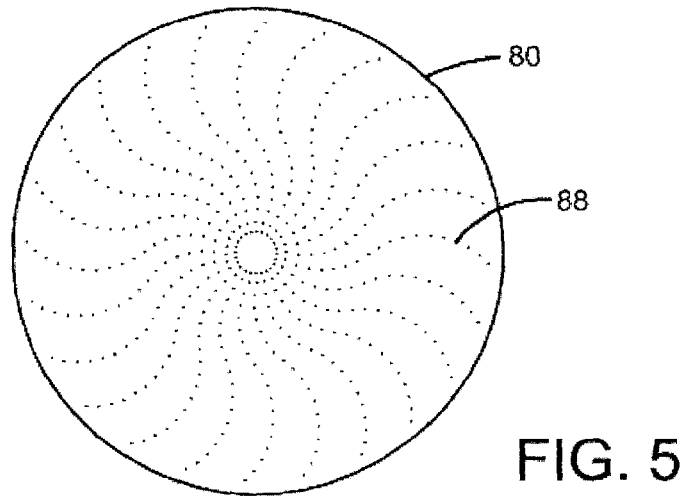
FIG. 5 is a schematic view of an orienter disc according to the present invention.

As shown in FIG. 5, the location of silica fiber tips 82 may be arranged in a pattern relative to orienter disc 80. In other embodiments, the pattern may be in spirals emanating from the center of orienter disc 80, for example a sunflower pod spiral. In other embodiments, the pattern may be in concentric rings emanating from the center of orienter disc 80. In other embodiments, a random arrangement of silica fiber tips is employed.

According to one embodiment, the silica fibers are used to return the captured light from the target to the CCD within spectrometer 10. In an embodiment these receiving cables 310 shall be arranged hexagonally around the emission fiber optic cable 309 which directs light originating from the laser emitter 21 (UV, Infrared, Fluorescence, or Raman, etc.). According to Utzinger and Richards-Kortum, a hexagonal arrangement of light capturing silica fibers 310 around the emission source 309 is an efficient means of capturing light from the target in Raman spectroscopy applications (Utzinger). The surfaces of the interior of the mouth and nose and the molecular remnants of consumed illegal or controlled substances are the targets of this invention.

In one or more embodiments, a single glass ball lens may be employed instead of the fluorescence blossom detector.

In one or more embodiments, blossom detectors may be employed around each laser emitting optical fiber (UV, Infrared, Fluorescence, or Raman, etc.), to capture scattered light from a plurality of angles.

In one or more embodiments, optical filters, lenses and gratings may be employed advantageously to optimize the emitted beam intensity as well as the signal strength of the returning beam via the optical fibers.

In another embodiment, utilizing the stand-off technique, such as the Mini-Raman Lidar System (MRLS) developed and field tested by the Brookhaven National Laboratory (BNL), at close distance, an independent freely moving focusing lens is directed autonomously or manually utilizing the targeting crosshair(s) to telescope/focus on one or more target surfaces illuminated by the laser source 21 (Sedlacek 2001). In an embodiment, the stand-off emission and collection technique would be employed in addition to the collection fiber optic heads which surround each laser emitting fiber optic cable and the fluorescence blossom detector which may inadvertently receive scattered light during the examination.

Figure 6:
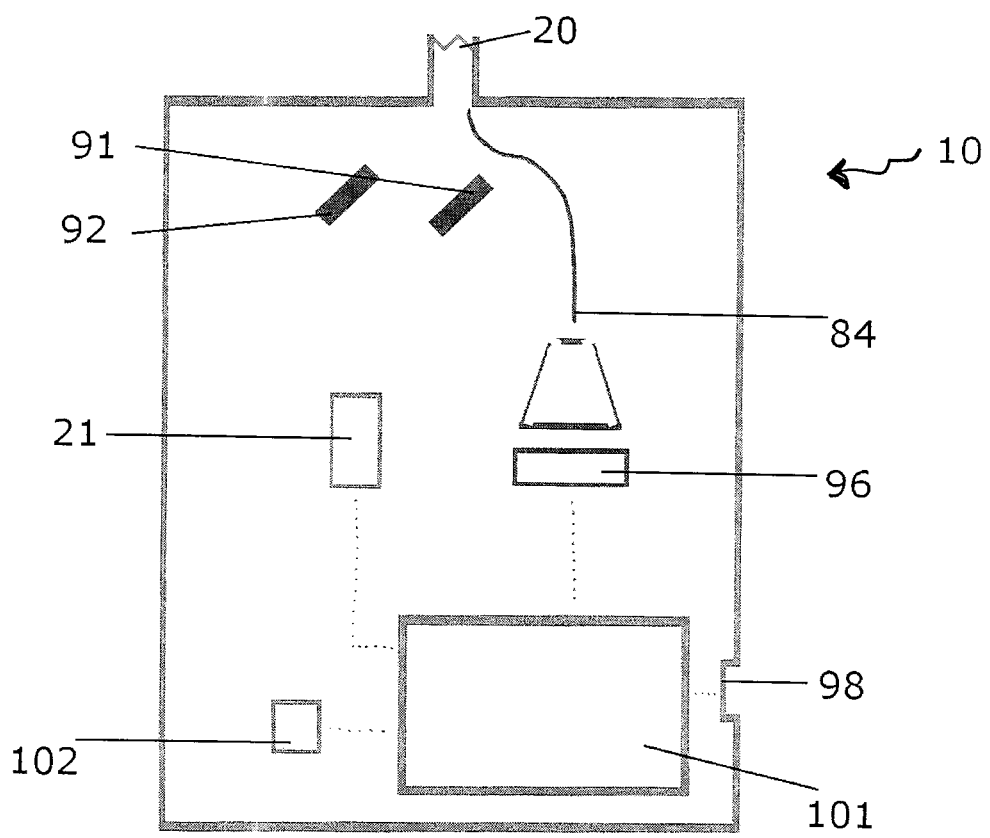
FIG. 6 is a schematic view of a spectrometer according to the present invention.

As shown in FIG. 6, spectrometer 10 includes mirrors 91, 92, excitation laser 21, CCD 96, USB port 98, computer 101, and optional GPS 102. Fiber optic bundles enter spectrometer 10 (shielded fiber optic bundle cover 84 shown) and the fiber optic strands are directed toward CCD 96. Data collected by CCD 96 is transferred to computer 101 for processing and storage.

According to an embodiment, once the fluorescence blossom detector and computer have established that fluorescent lighting conditions are within the acceptable range for an accurate examination, the excitation laser may be activated by the user of the device. Once the user has activated the examination via the touch screen user interface, the computer activates the excitation laser 21. The excitation beam is transmitted via the optical system such as that employed by U.S. Pat. No. 8,248,588 B2 and U.S. Pat. No. 8,300,220 B2. Within the mask the beam is collimated and conveyed to the fiber optic bundles leading to the spherical aiming apparatus. The collimated beam diameter corresponds to the diameter of the fiber optic bundle of emissions fiber optic cables in order to maximize the efficiency of the transmission and to preserve signal strength and intensity to the target. Within the spherical aiming apparatus, the receiving fiber optic cables are conjoined in hexagonal formation around the excitation fiber optic cables. According to the present embodiment, there are 7 emission fiber optic cables and 6 receiving fiber optic cables surrounding each emission cable. In an embodiment a variety of lenses may be employed at the head of these emission fiber optic cables to optimize signal for the purpose of examination and by collimating, focusing or dispersing the signal as desired in the embodiment. The receiving fiber optic heads then receive and transmit the back scattered light to the CCD. Each bundle of six fiber optic receiving cables then carries an individual beam to the CCD. Optional notch filter or other optical filtration may be employed. In the present embodiment, each bundle of hexagonally arranged receiving cables, a total of 7 bundles, is allotted a region of the surface of the CCD. The optical data collected by the CCD is then conveyed to the computer system which cross-references this optical data with the database of existing spectrometric signatures of illegal and controlled substances and biological analytes and indicators of illegal or prescription drug consumption. The computer also receives the optical data from the HD camera which is recorded with the results of the examination. These images will be archived with test results in order to provide an image of the target surfaces that produced a positive result for use in court proceedings. In an embodiment utilizing a continuous scanning method, the HD camera will record images throughout the scanning process in order to determine the target surface that produced the positive result. In another embodiment, the HD camera will utilize a separate CCD within the spherical aiming apparatus, such as those that are available in commercial digital cameras. Upon completion of the examination, the computer activates the camera flash and an HD digital photograph is produced in order to identify the test subject in court as well as to document any biological indicators of prolonged substance abuse for use as evidence in court proceedings.

In one or more embodiments, computer 101 of spectrometer 10 includes an internal computer hard disk containing a database of spectrometric signatures of known controlled and illegal substances, as well as current lists of analytes and biological indicators of drug consumption and intoxication. In one or more embodiments, data results detection-by-detection head 70 may be cross-referenced with these existing spectrometric signatures in order to determine a positive or negative result for the presence of controlled and illegal substances and biological indicators of drug consumption and intoxication.

In one or more embodiments, the device further includes a data encryption program for the secure transfer of information from law enforcement to other government agencies.

In one or more embodiments, the device further includes a global positioning system (GPS) microchip, so that the location and time of the test may be noted and recorded. In the event of a positive result, GPS data is transmitted to the computer system. In one or more embodiments, the device further includes a USB port. Data from the GPS may be conveyed to the internal computer, recorded, and optionally transmitted to other electronic devices via connection through the USB port.

In one or more embodiments, the device further includes a connector that is adapted to link the device to a smart phone, such as an iPhone® or other similar cellular device. In these or other embodiments, a GPS may be included in the cellular device.

Figure 7:
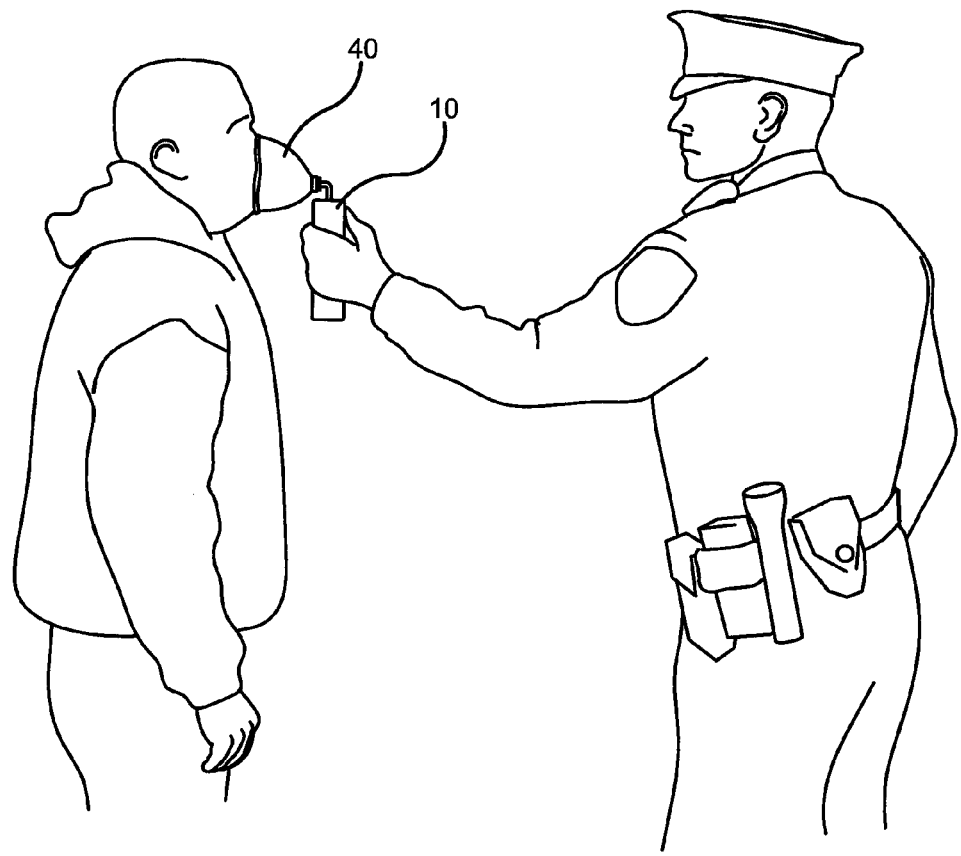
FIG. 7 is a perspective view of a device in use according to the present invention.

According to one embodiment, and as generally portrayed in FIG. 7, mask 40 fits over the mouth and nose of a human test subject, and prevents extraneous light, including florescent lighting from interfering with the examination, stabilizes the laser relative to the target surfaces and to ensure standard lighting conditions during the taking of digital photographs. Fluorescent lighting creates signal noise in the embodiment utilizing a Raman spectrometric laser source and sensors, which could compromise the integrity of the test results. According to one embodiment, a concave space to contain the laser head, spherical aiming apparatus 96 and silica fiber cables and lenses. Regardless of the degree to which florescent lighting conditions diminishes the validity of the test results, the presence of fluorescent lighting conditions could be used by a DUI defense attorney to cast doubt over the test results and/or to have the test results removed from the evidence against his/her client. Thus, a memory/contouring/form fitting mask to shield the laser and testing surfaces from extraneous fluorescent lighting conditions will give utility to law enforcement personnel practicing the device. In one or more embodiments, mask 40 is fabricated from polymeric material. The polymer selected should be characterized as robust, yet elastic to create a form fitting seal around the mouth and nose of the test subject. In one or more embodiments, mask 40 may be fabricated from a laminate that contains multiple layers. In one or more embodiments, at least one layer of the laminate is opaque to fluorescent light. In one or more embodiments, the laminate may include an opaque coating. Advantageously, the opaque coating scatters, blocks and/or reflects fluorescent light.

As described by Eckenrode, Brian A., Edward G. Bartick, Scott D. Harvey, Mark E. Vucelick, Bob W. Wright, Rebecca A. Huff, "Portable Raman Spectroscopy Systems for Field Analysis," FBI Forensic Science Communications Vol. 4 (October 2002), fiber optic probes may be used with commercially available Raman spectroscopic devices in order to meet the needs of a particular field application, such as in the identification of potentially hazardous materials. The silica fibers and a dichroic filter may be utilized to both transmit the laser frequency as well as to receive and transmit the back-scattered light through a long pass filter that transmits only Stokes-scattered light. Further, according to the same article, the length of the fiber optic tubing can be greater than 100 meters without compromising the validity of the examination results (Eckenrode 2002). According to Utzinger, Richards-Kortum's, "Fiber Optic Probes for Biomedical Optical Spectroscopy," optical filtration by long pass, notch or other optical filters and the use of a spectrograph, are commonly utilized in biomedical optical spectroscopic applications to optimize the laser emission and return signal to the detector/CCD (January 2003). Fiber optics shall be employed and arranged in variety of embodiments of the present invention and may employ long pass, notch, digital filtration and other means of optical filtration, as well as a spectrograph to optimize results of the examination.

For the purposes of this invention, the silica fibers will enable the user to adjust the direction and orientation of the laser light to the target surface utilizing an adjustable apparatus without having to alter the laser calibration or frequency, as Raman spectrometers are more accurate at closer distances. As described in Sedlacek et al., "Short-range, Non-contact Detection of Surface Contamination Using Raman Lidar," International Society for Optics and Photonics 4577, 95-104 (2001), Raman spectroscopic analysis experiences an accuracy curve relative to the distance from the target material, and from 1 meter is accurate to 0.5 grams (g), and at roughly a quarter of a meter distance is accurate to 0.007 g. According to another embodiment, other light filters may be employed in order to select and/or optimize the laser emission. In one or more embodiments, the frequency of the emission may also be selected and/or optimized through the use of a tunable laser source and/or optical filters.

According to one embodiment, spectrometer 10 includes or is in communication with a computer system that contains sufficient hard disk memory to store and utilize all software programs necessary to practice the device, all databases of spectrometric signatures, and all recorded data from the examination process. The computer system also may be hard-wired or wirelessly connected to other exterior devices or computer systems, such that data may be transferred from one device to another.

Method of Examination

In one or more embodiments, the present invention provides a method of examination. In one or more embodiments, the method includes the steps of:

1. The test subject is instructed to open his/her mouth agape; showing teeth.
2. The mask is placed over the mouth and nose.
3. The form-fitting mask is adjusted to prevent extraneous light from interfering with the examination, and the laser is disabled by the internal computer until the sensor indicates that the lighting conditions are acceptable for an accurate testing iteration.
4. Laser (e.g. UV, infrared, florescent, Raman) is aligned utilizing the crosshair(s) in the user interface display.
5. Device laser is activated and scans the test subject's teeth, gums, palate, back of throat, nasal passages and in vivo gases, mucus and other biological fluids for molecular remnants of consumed prescription, narcotic and illegal drugs and analytes and biological indicators of consumption of illegal or controlled substances.
6. High-resolution digital photographs are taken of the test subject's teeth, nasal passages, palate, tongue, gums for proof of proper alignment and accuracy of the examination and identification of the test subject in court.
7. Test results are catalogued in the database and cross-referenced with existing spectrometric signatures for immediate substance identification and displayed on the user interface.

According to one embodiment, the fluorescent blossom detector 76 receives light levels from within mask 40 prior to initiating the laser examination, and the light is directed via silica fiber strands 82 to the CCD. The CCD then creates and transmits a digital signal which is conveyed to the computer system within spectrometer 10. The computer compares the signal with a predetermined threshold of fluorescent light units to determine whether or not the fluorescent lighting conditions are acceptable to initiate the excitation laser 21 and the examination.

According to one embodiment, a user, such as a law enforcement official, maneuvers swiveling sphere 22 to direct the detector head 70 to align with the target surface, by utilizing a touch screen interface on spectrometer 10. According to this embodiment, the movement of the spherical aiming apparatus will correspond to the use of a targeting crosshair on the touch screen by the user, or other embodiments which control the orientation of and direct the laser light. According to one embodiment, the tube will be aligned to effectively illuminate the target surface, and may incorporate fiber optic tubing to both transmit the source laser energy and to receive the scattered light from the target material.

According to one embodiment, a light source or camera flash 318 to illuminate the interior of the test subject's mouth for the accurate taking of high definition digital photographs for use as evidence in the prosecution of DUI offenders. Sufficient light will be necessary to dispel the darkness of the interior of the test subjects mouth and nasal passages. This light source will ensure the fidelity of the high definition photographs.

According to one embodiment, the spectrometer may be a tabletop spectrometer. In this embodiment, the mask may be rigidly positioned at an angle above the table, such that the test subject may be seated, and is able to lean into the device, and place his or her face into the mask, which is flexible enough to conform to the contours of the face. All other procedures are followed as described above.

According to one embodiment, optical lenses are employed at the light-emitting fiber optic cable tips on the spherical aiming apparatus, in order to focus, disperse or collimate the laser light beam toward the target surface of the mouth or nasal passages.

According to one embodiment, all fiber optic lasers fire in a single iteration upon the command of the user, via a touch screen interface of the device. According to another embodiment, the lasers are utilized in a continuous, automated scan of the test subject's mouth and nasal passages. The imaging from the HD camera is cross-referenced with the continuous scan to ensure that the positive result was detected within the interior of the mouth and nasal passages and not the exterior such as the lips, epidermis, or nose. The location of the positive results is a vital distinction, as consumption of illegal and controlled substances must be proven by a positive result from the in vivo target surfaces.

REFERENCES

Amendments to the Constitution of the United States of America. www.gpo.gov U.S. Government Printing Office. http://www.gpo.gov/fdsys/pkg/GPO-CONAN-1992/pdf/GPO-CONAN-1992-7.pdf Cull, E. C., M. E. Gehm, B. D. Guenther, and D. J. Brady. "Standoff Raman Spectroscopy System for Remote Chemical Detection." International Society for Optics and Photonics. Vol. 5994, 59940H, (2005).

Drug Involvement of Fatally Injured Drivers: A Brief Statistical Summary. U.S. Department of Transportation, National Highway Traffic Safety Administration. (November 2010) http://www-nrd.nhtsa.dot.gov/Pubs/811415.pdf accessed on Mar. 5, 2013.

Eckenrode, Brian A., Edward G. Bartick, Scott D. Harvey, Mark E. Vucelick, Bob W. Wright, Rebecca A. Huff. Portable Raman Spectroscopy Systems for Field Analysis. FBI Forensic Science Communications. Volume 4. (October 2002). Peterson, Dan M. Drug Use & Oral Clues. Family Gentle Dental Care.

Sedlacek, Arthur J., Mark D. Ray, N. S. Higdon and D. A. Richter. "Short-range, Non-contact Detection of Surface Contamination Using Raman Lidar." International Society for Optics and Photonics 4577, 95-104 (2001).

U.S. Lighting Market Characterization: Volume 1, September 2002. Building Technologies Program Office of Energy Efficiency and Renewable Energy U.S. Department of Energy. http://apps1.eere.energy.gov/buildings/publications/pdfs/ssl/lmc_vol1_final.pdf Utzinger, Urs and Rebecca R. Richards-Kortum. "Fiber Optic Probes for Biomedical Optical Spectroscopy." Journal of Biomedical Optics 8(1), 121-147 (January 2003).

Tennessee Dental Hygienists Association. Substance Abuse: Considerations for the Oral Health Professional When the Client is Suspected to be Abusing Substances, available at http://www.tndha.org/ce_files/Chemical %20Dependency %20CE.pdf, accessed on Mar. 18, 2013.

We claim:

1. A portable device for instantaneous drug testing for a wide spectrum of drugs that does not require taking an invasive sample of breath or saliva from a test subject having a mouth and nose region, the device comprising:
   a flexible, form-fitting, opaque mask, adapted to fit snuggly over the mouth and nose region of a test subject who is suspected of drug use;
   a tube that is connected, at a first end, to the mask with a universal locking fastener, wherein the connection may be optionally reinforced with a locking ring;
   a swiveling sphere positioned inside the mask and bearing a detector head, wherein the detector head comprises a high definition camera, a source of light for illuminating a target surface within the mouth or nose of the test subject, a plurality of spectroscopic Raman fiber optic heads, and one or more fluorescence blossom detector heads;
   a spectrometer connected to a second end of the tube, said spectrometer comprising an internal computer, a CCD, an excitation laser, one or more mirrors, optical filters and a user interface that includes receivers for receiving input from a user, and a display for displaying to a user real-time images from the high definition camera and test results from the computer; and
   a plurality of fiber optic strands extending from the Raman fiber optic heads and fluorescence blossom detector heads, through said tube, into said spectrometer, where each strand is directed toward said CCD.

2. The device of claim 1, wherein said plurality of fiber optic strands include one or more light-emitting fiber optic cables to emit the source light.

3. The device of claim 1, wherein the spectrometer includes an ultraviolet, infrared, Raman, or fluorescence spectrometer, or a combination thereof.

4. The device of claim 1, wherein the user interface includes a touch screen interface.

5. The device of claim 1, wherein the computer is hardwired or wirelessly connected to other exterior devices or computer systems, such that data may be transferred from one device to another.

6. The device of claim 2, wherein the light-emitting fiber optic lasers on the sphere include optical lenses, in order to focus, disperse or collimate the laser light beam toward the target surface of the mouth or nasal passages.

7. A method for instantaneous testing in the field for a wide spectrum of drugs that does not require taking an invasive sample of breath or saliva, the method comprising the steps of:
   providing a test subject under suspicion of drug usage or an employee contractually subject to random drug screenings or any other field drug examination of a test subject;
   instructing the test subject to open his/her mouth, exposing the test subject's teeth, nasal passages, palate, tongue, back of throat and gums;

providing a portable device for instantaneous drug testing for a wide spectrum of drugs that does not require taking an invasive sample of breath or saliva, the device comprising:
- a flexible, form-fitting, opaque mask, adapted to fit snugly over the mouth and nose region of a test subject who is suspected of drug use;
- a tube that is connected, at a first end, to the mask with a universal locking fastener, wherein the connection may be optionally reinforced with a locking ring;
- a swiveling sphere positioned inside the mask and bearing a detector head, wherein the detector head comprises a high definition camera, a source of light for illuminating a target surface within the mouth or nose of the test subject, a plurality of fiber optic heads, an extraneous light sensor, and one or more fluorescence blossom detector heads;
- a spectrometer connected to a second end of the tube, said spectrometer comprising an internal computer, a CCD, an excitation laser, one or more mirrors, and a user interface that includes receivers for receiving input from a user, and a display for displaying to a user real-time images from the high definition camera and test results from the computer; and
- a plurality of fiber optic strands extending from the spectroscopic fiber optic heads and fluorescence blossom detector heads, through said tube, into said spectrometer, where each strand is directed toward said CCD;

placing the mask over the mouth and nose of the test subject;
adjusting the mask to eliminate extraneous light from entering the mask;
activating the extraneous light sensor to test for extraneous light, whereupon if no extraneous light is detected, or if the amount of extraneous light is less than a predetermined amount, a positive result is indicated by the device interface, and the method may proceed, and whereupon if the amount of extraneous light exceeds the predetermined amount, the device interface indicates the lighting conditions are not acceptable to conduct the examination and the laser is deactivated;
aligning the laser utilizing the crosshairs in the user interface display;
activating the laser;
scanning the test subject's teeth, gums, palate, back of throat, nasal passages and in vivo gases, mucus and other biological fluids;
collecting light emissions using the detector head;
transmitting the collected light emissions to the spectrometer;
analyzing, by using the computer, the emissions for indications of the molecular remnants of consumed prescription, narcotic and illegal drugs, and generating test results summarizing any positive indications;
photographing one or more of the test subject's teeth, nasal passages, palate, tongue, gums by using high-resolution digital photography, in order to record the proper alignment and accuracy of the method and to assist in identification of the test subject in possible later court proceedings;
displaying the test results on the user interface display;
storing the test results in the computer; and
optionally transmitting the test results to another electronic device, either wirelessly or via hard-wire connection to the USB port of the spectrometer.

8. The method of claim 7, wherein the method is performed by a law enforcement official.

9. The method of claim 8, wherein the method is performed during a traffic stop.

10. The method of claim 8, wherein the test subject is suspected of illegal drug use.

11. The method of claim 7, wherein all fiber optic lasers fire in a single iteration upon the command of the user, via a touch screen interface of the device.

12. The method of claim 7, wherein the fiber optic lasers fire in a continuous, automated scan of the test subject's mouth and nasal passages.

13. The method of claim 7, wherein the fiber optic cables are allotted individual regions on the surface of the CCD allowing the computer to determine which fiber grouping received the positive result and cross-referencing this data with the target image at the instant of the positive result.

14. The method of claim 7, wherein the method is performed for employment drug testing.

15. The device of claim 1, wherein the flexible, form-fitting, opaque mask is further adapted to prevent unnecessary or accidental exposure to laser light, and wherein the device further includes an extraneous light sensor within the mask, and a deactivation mechanism to deactivate the laser if extraneous light is sensed within the mask.

16. The device of claim 1, wherein the device is an extraoral drug detection device for in vivo examination of the interiors of the test subject's mouth, nose and throat.

17. The method of claim 7, wherein said step of analyzing further includes the step of analyzing, by using the computer, the emissions for indications of the molecular remnants of consumed alcohol.

18. The method of claim 7, wherein said step of analyzing does not include analysis for dental purposes.

19. The method of claim 7, wherein the method does not require contact with the target surface, does not remove a sample, and does not require sample preparation or the use of chemical reagents.

20. The method of claim 7, wherein the method is useful for detection of biological analytes, including drug metabolites.

* * * * *